United States Patent [19]
Garcia

[11] Patent Number: 5,722,962
[45] Date of Patent: Mar. 3, 1998

[54] TROCAR PORT FILTER

[76] Inventor: Joxel Garcia, 64 Brook Ridge Dr., Avon, Conn. 06001

[21] Appl. No.: 581,052

[22] Filed: Dec. 29, 1995

[51] Int. Cl.⁶ ................................................ A61M 25/00
[52] U.S. Cl. ............................ 604/264; 604/164; 606/185
[58] Field of Search ........................ 604/19, 21, 22–26, 604/27–29, 33, 35, 44, 45, 51, 54, 117, 118, 126, 164, 165–170, 172, 239, 264, 272, 273, 274, 317–320; 128/747, 754; 606/185, 167; 95/273, 286

[56] References Cited

U.S. PATENT DOCUMENTS

| | | | |
|---|---|---|---|
| 4,144,040 | 3/1979 | Claes et al. | 55/97 |
| 4,459,139 | 7/1984 | vonReis et al. | 55/189 |
| 4,535,773 | 8/1985 | Yoon. | |
| 4,735,603 | 4/1988 | Goodson et al.. | |
| 5,066,288 | 11/1991 | Deniega et al.. | |
| 5,098,375 | 3/1992 | Baier. | |
| 5,199,944 | 4/1993 | Cosmescu. | |
| 5,246,419 | 9/1993 | Absten. | |
| 5,258,127 | 11/1993 | Gsell et al. | 210/767 |
| 5,290,237 | 3/1994 | Verkaart | 604/126 |
| 5,300,084 | 4/1994 | Johnson. | |
| 5,360,396 | 11/1994 | Chan. | |
| 5,411,474 | 5/1995 | Ott et al.. | |
| 5,578,000 | 11/1996 | Greff et al. | 604/22 |

*Primary Examiner*—Corrine M. McDermott
*Assistant Examiner*—Cris L. Rodriguez
*Attorney, Agent, or Firm*—Pepe & Hazard LLP

[57] ABSTRACT

A trocar assembly for exhausting gas from a body cavity comprises a trocar having a housing with a flow passage therethrough which terminates in an outlet fitting, and a filter mounted thereon. The filter includes a housing with a chamber, and an inlet and an outlet which communicate with opposite sides of the chamber to provide a flow passage therethrough. About the inlet is a fitting and there is a means on the inlet fitting mounting the filter on the outlet fitting of the trocar housing. Within the chamber is a filter means so that effluent gas passing through the trocar flow passage flows through the filter means prior to exiting through the outlet of the filter.

13 Claims, 1 Drawing Sheet

TROCAR PORT FILTER

BACKGROUND OF THE INVENTION

The present invention relates generally to trocars for exhausting insufflation gases from an abdominal cavity and, more particularly, to a filter for mounting on a trocar vent port.

Recent developments in laparoscopic and endoscopic surgery have resulted in the increasing usage of insufflation with suitable gas, such as carbon dioxide $CO_2$, to inflate the abdominal cavity like a balloon by expanding the peritoneum to bulge outwardly and separate from the organs inside the cavity as well as to separate the organs. The insufflation increases the working area for the surgeon in the normally confined abdominal cavity and allows better viewing within the cavity and instruments to be manipulated in the abdominal cavity with less obstruction.

After such insufflation, an obturator, which is a sharp pointed instrument, is inserted into the cannula of a trocar to puncture the peritoneum with a lower risk of injuring organs. Thereafter, the obturator is withdrawn and a laparoscopic or endoscopic surgical instrument is inserted through the cannula to perform the desired surgery.

A conventional system used for introducing the insufflation gases into the abdominal cavity includes a pneumoperitoneum needle connected to a gas source through a flexible conduit such as surgical rubber tubing.

Another technique of insufflating the body cavity connects a source of pressurized gas to a valve fitting on the trocar through which, when opened, the pressurized gas may enter into the body cavity through the trocar cannula to insufflate the cavity. After the conduit has been insufflated with gas, the valve may be closed to seal the trocar passage, and the gas source may be removed from the valve fitting.

After abdominal surgery is completed, the gas used to inflate the abdominal cavity must be vented from the abdominal cavity. One technique for venting these gases employs the use of a suction pump connected to a needle inserted into the cavity. An easier technique preferred by some surgeons is similarly to vent these gases through the trocar by releasing the valve on the housing of the trocar, and venting the gases to the surrounding atmosphere. However, these gases may carry bacteria, viruses, body fluids, etc., and, if unfiltered, these may be dispersed in the environment of the operating room suite, thereby increasing the chances of contamination of operating room personnel and the patient.

It is an object of the present invention to provide a novel trocar port filter which prevents the outflow of particulate matter, microorganisms, and body fluids into the operating room, while allowing insufflation gases to flow out of the abdominal cavity at a high flow rate.

It is also an object to provide such a filter which is relatively simply and quickly installed on the trocar port in an effective sealed engagement.

Another object is to provide a filter which may be fabricated relatively easily and economically to enhance its usage as a disposable filter.

SUMMARY OF THE INVENTION

It has now been found that the foregoing and related objects may be readily attained in a trocar assembly for exhausting gas from a body cavity comprising a trocar having a housing with a flow passage which terminates in an outlet fitting, and a filter mounted thereon. The filter includes a housing providing a chamber, an inlet and an outlet communicating with opposite sides of the chamber to provide a flow passage therethrough, and a fitting about the inlet. The filter is coupled to the trocar by coupling means on the inlet of the filter housing and on the fitting of the trocar housing. Within the chamber is a filter means so that effluent gas passing through the trocar flow passage flows through the filter means prior to exiting through the outlet of the filter.

Generally, the filter mounting means includes a resilient mounting member which has a passage through it. The passage has an inlet portion mounted and sealed on the outlet fitting of the trocar housing and an outlet portion mounted and sealed on the inlet fitting of the filter housing. Conveniently, the resilient mounting member is tubular.

Preferably, the trocar housing includes a valve to selectively open and close the flow passage therethrough. Normally, the filter means includes a first filter element adjacent the inlet to filter relatively large particles and a second filter element oriented adjacent the outlet to filter relatively fine particles. These filter elements are generally hydrophobic.

Preferably, the housing of the filter includes a pair of interengaging housing elements which have a base wall and a sidewall extending about their periphery. The base walls of these housing elements also have fittings about the inlet and outlet and are generally fabricated from synthetic resin.

BRIEF DESCRIPTION OF THE PREFERRED EMBODIMENTS

DETAILED DESCRIPTION OF THE PREFERRED EMBODIMENT

Figure 1:
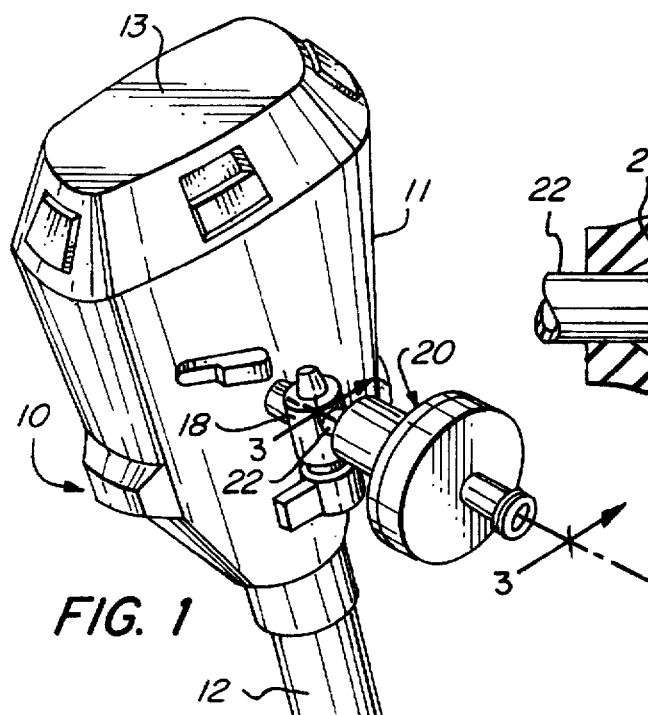
FIG. 1 is a perspective view of a trocar partially inserted into the abdominal cavity shown in phantom line of a fragmentarily illustrated patient and incorporating a trocar port filter embodying the present invention.

Turning first to FIG. 1, therein illustrated is a trocar generally designated by the numeral 10 having a housing 11 at one end and a tubular cannula 12 extending therefrom. A removable obturator 14 is telescopically mounted within the cannula 12 and extends beyond a distal portion of the cannula 12 into the abdominal cavity to initially pierce the peritoneal wall 16 of the cavity of a patient undergoing laparoscopic or endoscopic surgery. The proximal end of the obturator 14 is connected to the cover 13 of the housing 11. After piercing the peritoneal wall 16, the obturator 14 may be telescopically retracted from the lumen of the cannula 12 by releasing and lifting the housing cover 13.

In order to insufflate the body cavity 16, a source of pressurized gas (not shown) is connected to a fitting 22 on the valve 18 of the trocar 10 through which, when opened, the pressurized gas may enter into the interior of the housing 11 and cannula 12, to insufflate the abdominal cavity. After the peritoneal cavity has been properly insufflated, the valve 18 is closed to seal the trocar 10, and the gas source may be removed from the trocar value fitting 22. The trocar cannula 12 and housing 11 are sealed to prevent the gas in the body from escaping through the trocar. When it is desired to exhaust the gas from the abdominal cavity, a filter embodying the present invention and generally designated by the numeral 20 is connected to the trocar valve fitting 22, and the valve 18 is opened to vent the gas through the valve 18 and the filter 20.

Figure 3:
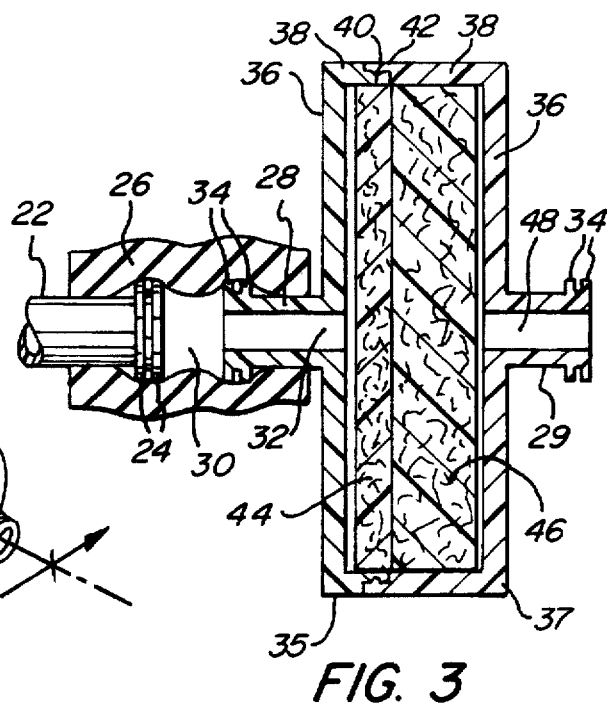
FIG. 3 is a sectional view of the filter along the line 3—3 of FIG. 1, showing the filter attached to the trocar port fitting and drawn to a greatly enlarged scale.
Figure 2:
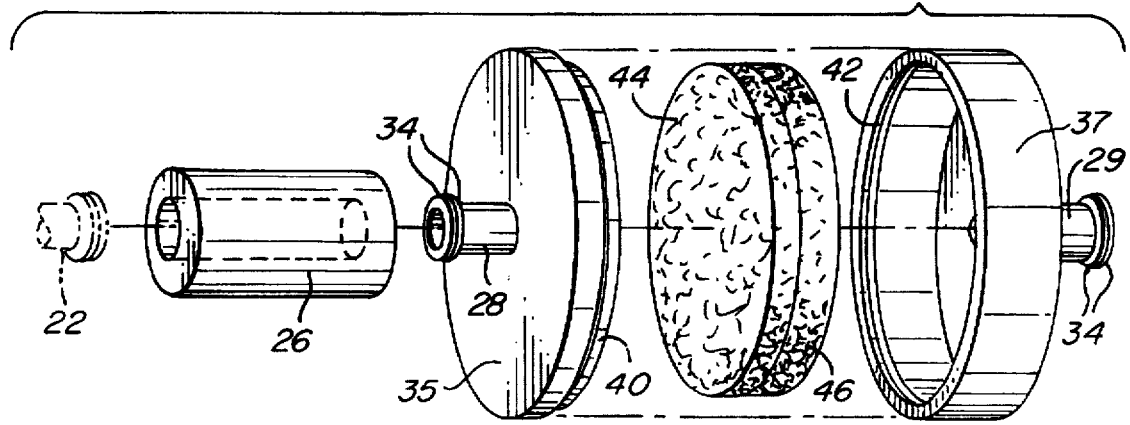
FIG. 2 is an exploded view of the filter and a fragmentarily illustrated outlet port fitting of the trocar.

Turning in detail to FIGS. 2 and 3, the filter 20 includes a flexible pair of casing elements 35, 37 providing a housing with a cavity therein and a pair of hydrophobic filter elements 44, 46, seated in the cavity. Each casing element 35, 37 has a base wall 36 and a sidewall 38 extending about its periphery. The end portions 40, 42 of the two sidewalls 38 of the elements 35, 37, respectively, snap fit to form the housing as seen in FIG. 3. The end portion 40 of the casing element 35 is resiliently deflectable and seats within the end portion 42 of the casing element 37 which is also resiliently deflectable. The base walls 36 have a coaxial aperture therein providing respectively, an inlet 32 and an outlet 48, and cylindrical fittings 28, 29 extend outwardly about the inlet 32 and outlet 48 respectively to provide a flow passage through the filter. The fittings 28, 29 each have a collar 34 about their outer end with a peripheral groove therein.

The filter elements 44, 46 are disc-shaped and extend across the full diameter of the casing elements 35, 37 to ensure complete filtration of the exhaust gases passing through the filter 20. The filter element 44 is positioned adjacent the inlet 32 of the filter 20, and filters relatively large particles while the filter element 46 adjacent the outlet of the filter 20 filters the smaller particles which pass though the first filter element 44. Using two types of filter elements further ensures the proper filtering of vented insufflation gases and reduces the possibility of clogging the filter 20.

Figure 4:
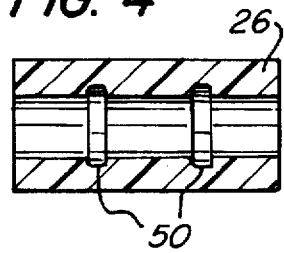
FIG. 4 is a sectional view of the resilient mounting member of the filter.

The filter 20 may be removably mounted upon the trocar port fittings 22 by the resilient coupling 26 as shown in FIG. 3. As shown in FIG. 4, the coupling 26 has an annular passage 30 through its center and two peripheral grooves 50 are provided adjacent each end of the passage 30. The grooves 50 seat the two collars 24, at the ends of the trocar value fitting 22 and the two collars 34 at the end of the filter fitting 28, respectively, to provide an airtight seal between the filter 20 and the trocar 10 and retain the fittings 22, 28 therein. The flexibility of the coupling 26 enables it to accommodate reasonable dimensional variation in the trocar fittings 22.

As will be appreciated, various materials may be employed for the construction of the filter housing. Most conveniently, the casing elements are molded from a synthetic resin such as polypropylene which is resiliently deflectable, relatively inexpensive to mold, and durable.

The filter elements 44, 46 may be made from suitable material which will not be quickly blocked or saturated by vapors exiting the abdominal cavity. Thus, the elements 44, 46 are preferably hydrophobic filters and may be fabricated from a polytetrafluoroethylene (PTFE) material and should serve to filter particulate matter of a size ranging from about 0.2 microns to about 0.5 microns.

The relatively inexpensive cost of the filter of the present invention allows it to be disposable and thereby eliminates the possibility that a clogged, inactivated or poorly effective filter may be used in a subsequent laparoscopic procedure.

Thus, it can be seen from the foregoing detailed description and the attached drawings that the novel trocar port filter of the present invention effectively prevents contamination by particulate matter in venting gases without the use of a vacuum pump or the like. The coupling of the filter may be readily and quickly installed onto the coupling trocar port fitting, and the filter can be readily removed and disposed.

Having thus described the invention, what is claimed is:

1. A trocar assembly for exhausting gas from a body cavity comprising:

(a) a trocar having a housing with an outlet fitting thereon and providing a flow passage through said trocar and in communication with said outlet fitting; and, (b) a filter mounted on said outlet fitting of said trocar and having (i) a housing providing a chamber, a flow passage through said housing, and an inlet and an outlet on said housing at opposite ends of said passage communicating with said chamber, said housing also having a fitting about said inlet;

(ii) means on said inlet of said filter housing mounting said filter on said fitting of said trocar housing, said mounting means including a resilient mounting member providing a passage therethrough, said mounting member having inlet and outlet portions, said inlet portion being mounted on said outlet fitting of said trocar housing in sealing engagement therewith and said outlet portion being mounted on said inlet fitting of said filter housing in sealing engagement therewith;

(iii) filter means in said chamber, whereby effluent gas passing through said trocar flow passage flows through said filter means prior to exiting said filter through said outlet thereof.

2. The trocar assembly according to claim 1 wherein said resilient mounting member is tubular.

3. The trocar assembly according to claim 1 wherein said trocar housing includes a valve to selectively open and close said flow passage therethrough.

4. The trocar assembly according to claim 1 wherein said filter means includes a first filter element adjacent said inlet to filter relatively large particles and a second filter element oriented adjacent said outlet to filter relatively fine particles.

5. The trocar assembly according to claim 4 wherein said first and second filter elements are hydrophobic.

6. The trocar assembly according t0 claim 1 wherein said housing of said filter includes a pair of interengaging housing elements, each of said housing elements having a base wall and a sidewall extending about the periphery thereof, said base walls of said housing elements having fittings thereon about said inlet and outlet.

7. The trocar assembly according to claim 6 wherein said housing elements are fabricated from synthetic resin.

8. A filter assembly for filtering exhaust gas from a body cavity through an associated trocar having an outlet fitting, said filter assembly comprising:

(a) a housing providing a chamber, a flow passage through said housing, and an inlet and an outlet on said housing at opposite ends of said passage communicating with said chamber, said housing also having a fitting about said inlet;

(b) a resilient mounting member providing a passage therethrough, said mounting member having inlet and outlet portions, said inlet portion being adapted to be mounted on the outlet fitting of an associated trocar housing and said outlet portion being mounted on said inlet fitting of said filter housing; and, (c) filter means in said chamber, whereby effluent gas passing through the associated trocar flows through said filter means prior to exiting said filter through said outlet thereof.

9. The filter assembly according to claim 8 wherein said resilient mounting member is tubular.

10. The filter assembly according to claim 8 wherein said filter means includes a first filter element adjacent said inlet to filter relatively large particles and a second filter element oriented adjacent said outlet to filter relatively fine particles.

11. The filter assembly according to claim 10 wherein said first and second filter elements are hydrophobic.

12. The filter assembly according to claim 8 wherein said housing of said filter includes a pair of interengaging housing elements, each of said housing elements having a base wall and a sidewall extending about the periphery thereof, said base walls of said housing elements having fittings thereon about said inlet and outlet.

13. The filter assembly according to claim 12 wherein said housing elements are fabricated from synthetic resin.

* * * * *